Aug. 14, 1962 J. B. ROBISON Plant Pat. 2,163
PEACH TREE
Filed Sept. 19, 1961
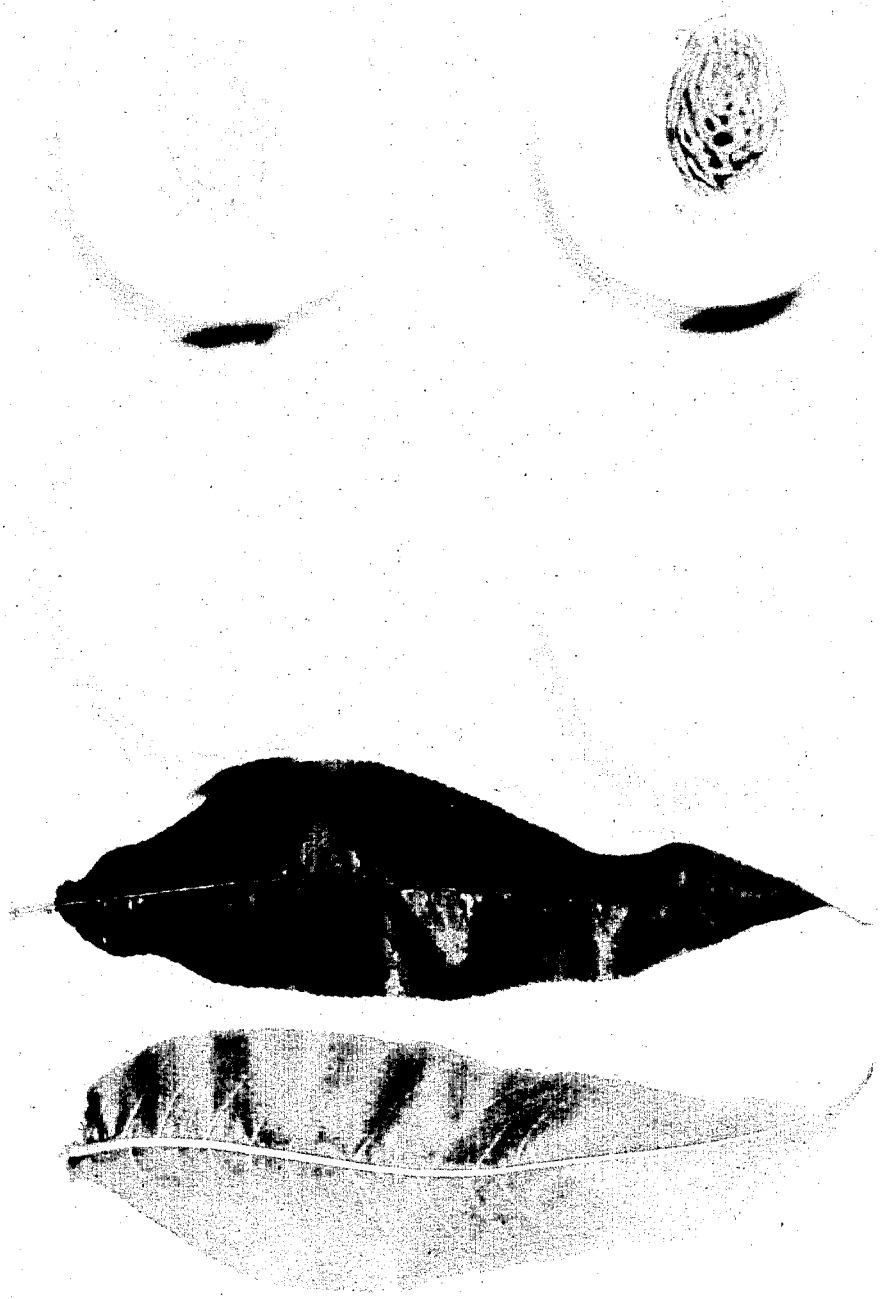
INVENTOR.
JOHN B. ROBISON
BY
ATTORNEY United States Patent Office Plant Pat. 2,163
Patented Aug. 14, 1962

2,163
PEACH TREE

John B. Robison, Rte. 1, Greer, S.C.

Filed Sept. 19, 1961, Ser. No. 139,322
1 Claim. (Cl. 47—62)

This invention relates to a new and distinct variety of peach tree.

The fruit of the new and distinct variety of peach tree is characterized especially by its most attractive appearance and good eating qualities, which are especially desirable at the ripening season of this peach variety as other varieties are scarce. This variety ripens after the J. H. Hale peach (unpatented) and a few days before the Rio Oso Gem peach (United States Plant Patent No. 84). The fruit is extremely attractive, having bright red cheeks and having a bright golden ground color diffused with red. It is symmetrical in shape and smooth, having a smooth suture line, and having less tendency to flatten than the Rio Oso Gem. Its flavor is that of a sweet mild peach with firm but melting flesh texture. Late mid-season peaches have a tendency to have excessive red around the pit and such red is not excessive in the fruit of the subject tree. The flesh of the peach is light yellow and its stone is of the free type. Another characteristic is that the fruit tends to non-browning of the flesh.

The new variety of peach tree was found by me as, what is thought by me to be, a chance seedling in a block of Dixired peach trees (unpatented) in my cultivated orchard seven and one-half miles southeast of Greer, South Carolina, on the Woodruff Highway. The tree has been asexually reproduced by me by being top-worked by budding (grafting) on Redhaven peach trees (unpatented) at my experimental orchard adjacent my home in the Woods Chapel community five miles southeast of Greer, South Carolina. Such asexual reproductions, at maturity and when in bearing, have been found to run true to the parent tree in all respects.

The accompanying drawing, in the form of a photograph, shows typical specimens of the leaves and fruit of my new variety of peach tree with the upper and lower surfaces of the leaves being illustrated and with both exterior and sectional views of the fruit being shown, all depicted in color as nearly true as it is reasonably possible to make the same in a color illustration of this character.

The following is a detailed description of the characteristics of my new variety as based upon observations of specimens grown at my orchard referred to above, with color terminology in accordance with Munsell's Book of Color, Munsell Color Company, Baltimore, Maryland, 1929–1960, except where general color terms of ordinary dictionary significance are obvious.

Tree:
- *Size.*—Medium.
- *Vigor.*—Average.
- *Growth.*—Slightly more spreading than upright.
- *Density.*—Medium.
- *Form.*—Globular to conical.
- *Hardiness.*—Average.
- *Production.*—Average to heavy.
- *Bearing.*—Good and regular.

Trunk:
- *Size.*—Medium.
- *Texture.*—Medium.

Branches:
- *Size.*—Medium.
- *Texture.*—Medium.
- *Color.*—Brownish to gray.
- *Lenticels.*—Scarce to medium number, medium to large in size.

Leaves:
- *Size.*—Medium. Average length 7". Average width 1⅞".
- *Form.*—Lanceolate, acuately pointed.
- *Thickness.*—Medium.
- *Texture.*—Smooth to slightly crinkled along midrib.
- *Margin.*—Serrate.
- *Petiole.*—Average length 7/16", medium thickness.
- *Glands.*—Reniform occurring mostly on base of petiole, sometimes one opposite, sometimes two opposite and occasionally one gland on the leaf blade.
- *Stipules.*—Inconspicuous.
- *Color (mature leaves).*—Top side—hue 7.5GY 3/4. Under side—hue 5GY 4/4.

Flower buds:
- *Hardiness.*—Medium.
- *Size.*—Medium.
- *Length.*—Medium.
- *Form.*—Plump.
- *Pubescence.*—Medium.

Flowers:
- *Blooming period.*—Midseason indicating medium chilling requirements.
- *Size.*—Large showy.
- *Color.*—Pink.

Fruit:
- *Maturity when described.*—Eating ripe.
- *First picking.*—August 11, 1961.
- *Last picking.*—August 22, 1961.
- *Size.*—Medium to large, fairly uniform. Average transversely in suture plane 2⅝" to 2⅞". Average diameter axially 2⅝" to 2⅞".
- *Form.*—Uniform, symmetrical, globose to slightly elongated.
- *Suture.*—Distinct, shallow and extends slightly beyond the apex showing slight depression beyond pistil point.
- *Ventral surface.*—Rounded.
- *Cavity.*—Elongated on suture plane with suture not showing on ventral side.
- *Base.*—Oblique to rounded.
- *Apex.*—Short.
- *Pistil point.*—Depressed to slightly raised.

Skin:
- *Thickness.*—Medium.
- *Texture.*—Medium.
- *Tendency to crack.*—None.
- *Down.*—Light and short.
- *Color.*—Cheek hue 5R 5/12–4/14. Ground hue 10YR 8/8.

Flesh:
- *Juice.*—Slightly dry.
- *Texture.*—Firm but melting.
- *Fibers.*—Slightly fibrous but tender.
- *Ripens.*—Evenly.
- *Flavor.*—Subacid with slight indication of soluble tannin tending to lend full bodied flavor.
- *Aroma.*—Normal peach aroma.
- *Eating quality.*—Very good to best.
- *Color.*—Hue 10YR 8/8.
- *Surface of pit cavity.*—Red with yellowish red fibers.

Stone:
- *Type.*—Free.
- *Size.*—Small to medium. Average length 1 7/16" to 1½". Average breadth 1" to 1⅛". Average thickness ¾" to 1 1/16".
- *Form.*—Flattened.
- *Base.*—Straight.
- *Sides.*—Unequal.
- *Surface.*—Regularly furrowed and pitted throughout.

*Ridges.*—Usually rounded toward base on either side but sometimes slight jagged.
*Pits.*—Elongated.
*Tendency to split.*—None.
*Color.*—Hue 5R 4/14.
Use: Market, dessert, canning.
Keeping quality: Good.
Shipping quality: Good.

The tree and its fruit herein described may vary in slight detail due to climatic and soil conditions under which the variety may be grown.

What is claimed is:

A new and distinct variety of peach tree substantially as shown and described characterized particularly as to novelty by fruit having the combination of a late ripening season after the J. H. Hale peach and a few days before the Rio Oso Gem peach, a most attractive form being slightly elongated from apex to cavity, having a bright red cheek and bright golden ground color diffused with red, and a smooth suture line, a most delicious flavor subacid with slight indication of soluble tannin tending to lend full bodied flavor, and tendency to non-browning of the flesh.

No references cited.